(12) United States Patent
Takahashi et al.

(10) Patent No.: US 9,890,114 B2
(45) Date of Patent: Feb. 13, 2018

(54) UREA SYNTHESIS METHOD (71) Applicant: TOYO ENGINEERING CORPORATION, Chiba (JP)

(72) Inventors: Masashi Takahashi, Chiba (JP); Eiki Nagashima, Chiba (JP)

(73) Assignee: TOYO ENGINEERING CORPORATION, Chiba (JP)

( * ) Notice: Subject to any disclaimer, the term of this patent is extended or adjusted under 35 U.S.C. 154(b) by 0 days.

(21) Appl. No.: 14/950,325

(22) Filed: Nov. 24, 2015

(65) Prior Publication Data

US 2016/0075642 A1    Mar. 17, 2016

Related U.S. Application Data

(63) Continuation-in-part of application No. PCT/JP2014/064159, filed on May 28, 2014.

(30) Foreign Application Priority Data

May 28, 2013 (JP) ................................. 2013-112144

(51) Int. Cl.
*C07C 273/04* (2006.01)
*B01J 19/02* (2006.01)
(Continued)

(52) U.S. Cl.
CPC ............. *C07C 273/04* (2013.01); *B01J 19/02* (2013.01); *C22C 38/00* (2013.01); *C22C 38/001* (2013.01);
(Continued)

(58) Field of Classification Search
CPC ..... C07C 273/04; C22C 38/001; C22C 38/44; C22C 38/04; C22C 38/02; C22C 38/58; C22C 38/00; B01J 19/02
(Continued)

(56) References Cited

U.S. PATENT DOCUMENTS 2,680,766 A    6/1954  de Ropp et al.
2,727,069 A  * 12/1955  Van Waes ............. C07C 273/04
                                                                562/555
(Continued)

FOREIGN PATENT DOCUMENTS

CN       1180071 A     4/1998
CN     101679224 A     3/2010
(Continued)

OTHER PUBLICATIONS

NIST ("Composition of Air, Dry (Near Sea Level)", p. 1, downloaded from < http://physics.nist.gov/cgi-bin/Star/compos.pl?matno=104 > on Sep. 9, 2016).*
(Continued)

*Primary Examiner* — Jafar Parsa
*Assistant Examiner* — Amy C Bonaparte
(74) *Attorney, Agent, or Firm* — Manatt, Phelps & Phillips, LLP (57) ABSTRACT

There is provided a urea synthesis method having excellent reliability and productivity with the amount of oxygen used as a corrosion-resistant agent minimized without using special duplex stainless steel. In a urea synthesis apparatus having a synthesis tower, a stripper, and a condenser, general-purpose austenitic-ferritic duplex stainless steel with Cr content: 21 to 26 wt %, Ni content: 4.5 to 7.5 wt %, Mo content: 2.5 to 3.5 wt %, N content: 0.08 to 0.30 wt %, C content: 0.03 wt % or less, Si content: 1.0 wt % or less, Mn content: 2.0 wt % or less, P content: 0.04 wt % or less, and S content: 0.03 wt % is used as a urea synthesis apparatus material in at least some of parts where the urea synthesis apparatus comes into contact with a fluid having corrosiveness, and oxygen feed concentration with respect to carbon dioxide is 100 to 2,000 ppm.

5 Claims, 6 Drawing Sheets (51) Int. Cl.
*C22C 38/00* (2006.01)
*C22C 38/58* (2006.01)
*C22C 38/02* (2006.01)
*C22C 38/04* (2006.01)
*C22C 38/44* (2006.01)

(52) U.S. Cl.
CPC .............. *C22C 38/02* (2013.01); *C22C 38/04* (2013.01); *C22C 38/44* (2013.01); *C22C 38/58* (2013.01)

(58) Field of Classification Search
USPC .......................................................... 564/68
See application file for complete search history.

(56) References Cited

U.S. PATENT DOCUMENTS

| | | | |
|---|---|---|---|
| 3,137,724 | A | 6/1964 | Guyer et al. |
| 3,488,293 | A * | 1/1970 | Hong ........................ C01C 1/12 148/284 |
| 4,208,347 | A | 6/1980 | Pagani |
| 4,504,679 | A | 3/1985 | Inoue et al. |
| 4,758,311 | A * | 7/1988 | Pagani ................... C07C 273/04 159/47.2 |
| 5,582,656 | A | 12/1996 | Kangas et al. |
| 5,936,122 | A * | 8/1999 | Kojima ................ B01D 5/0063 564/67 |
| 6,093,850 | A | 7/2000 | Kojima et al. |
| 2003/0155046 | A1 | 8/2003 | Yamadera |
| 2005/0107570 | A1 | 5/2005 | Saitou et al. |
| 2006/0073086 | A1 | 4/2006 | Sakai et al. |
| 2010/0217041 | A1 | 8/2010 | Carlessi et al. |
| 2013/0216449 | A1 | 8/2013 | Dieltjens |

FOREIGN PATENT DOCUMENTS

| | | | |
|---|---|---|---|
| EP | 0096151 | B1 | 7/1986 |
| EP | 1688511 | A1 | 8/2006 |
| GB | 1153107 | A | 5/1969 |
| GB | 1192044 | A | 5/1970 |
| GB | 1287710 | A | 9/1972 |
| GB | 1341497 | A | 12/1973 |
| JP | 53-149930 | A | 12/1978 |
| JP | 56-131558 | A | 10/1981 |
| JP | 58067661 | A | 4/1983 |
| JP | 59027863 | A | 2/1984 |
| JP | 01555735 | A | 9/1985 |
| JP | 60-209555 | A | 10/1985 |
| JP | 10182587 | A | 7/1998 |
| JP | 11180942 | A | 7/1999 |
| JP | 2003301241 | A | 10/2003 |
| JP | 2005097429 | A | 4/2005 |
| JP | 2006102590 | A | 4/2006 |
| JP | 2012207295 | A | 10/2012 |
| WO | 199500674 | A1 | 1/1995 |
| WO | 200301861 | A1 | 3/2003 |
| WO | 2008141832 | A1 | 11/2008 |
| WO | 2011162610 | A1 | 12/2011 |
| WO | WO 2011162610 | * | 12/2011 |
| WO | WO 2014192823 | * | 4/2014 |

OTHER PUBLICATIONS

NAS ("North American Stainless", p. 1-8, downloaded from < http://www.northamericanstainless.com/wp-content/uploads/2010/10/Grade-316-316L1.pdf > on Sep. 9, 2016).*

British Stainless Steel ("Chemical compositiosn of AISI (ASTM/ASME) and UNS duplex stainless steel grades" p. 1-3, downloaded from < http://www.bssa.org.uk/topics.php?article=182> on Sep. 9, 2016).*

By IMOA ("Practical Guidelines for the Fabrication of Duplex Stainless Steels", p. 1-68, downloaded from < http://www.imoa.info/download_files/stainless-steel/Duplex_Stainless_Steel_3rd_Edition.pdf> on Sep. 9, 2016).*

Office Action and Search Report issued by the State Intellectual Property Office of the People's Republic of China dated Sep. 5, 2016 for China Patent Application No. 2014800308551.7.

* cited by examiner

UREA SYNTHESIS METHOD

RELATED APPLICATIONS

This application is a continuation-in-part application of, and claims priority to, PCT application number PCT/JP2014/064159 filed May 28, 2014 (International Publication number WO2014/192823), which claims priority to JP Patent Application 2013-112144 filed May 28, 2013, all of which are hereby incorporated by reference.

TECHNICAL FIELD

The present invention relates to a method of synthesizing urea from ammonia and carbon dioxide while forming a passivation film on a metal surface inside an apparatus with oxygen.

BACKGROUND ART

Urea is an important raw material for a nitrogen-based fertilizer, one of three major elements essential for the growth of plants, and has supported food production in the world from old times. Even now, increased fertilizer production corresponding to increased food production accompanying population increase in the emerging countries of the world is required, and the construction of a urea synthesis apparatus based on a urea synthesis method having excellent reliability and productivity is an important problem.

Here, the reliability mainly refers to the property of protecting the metal surface inside this apparatus from ammonium carbamate produced as a reaction intermediate when urea is synthesized from ammonia and carbon dioxide, having strong corrosiveness to metal. On the other hand, the productivity refers to not only increasing the yield of the reaction of ammonia and carbon dioxide but a reduction in total urea production cost including a reduction in apparatus construction cost and a reduction in running cost with improved operating conditions.

Technical development for increasing such reliability and productivity has been mainly addressed from three viewpoints. The first is a chemical viewpoint that a passivation film is formed on the metal surface of the apparatus to increase corrosion resistance. The second is a material viewpoint that corrosion resistance to ammonium carbamate is enhanced by an improvement in the apparatus material itself. The third is a process viewpoint that improvements in corrosion resistance and reaction yield by improvements in the production process and the apparatus are promoted. But, these are in a conflicting relationship with each other, and a balanced urea synthesis method is required even now.

First, various techniques for forming a passivation film on a metal surface have been studied such as methods using oxidants such as oxygen, nitric acid, hydrogen fluoride, hydrogen peroxide, ammonium nitride, and ozone as disclosed in U.S. Pat. Nos. 2,680,766, 2,727,069, 3,137,724, British Patent No. 1,153,107, European Patent No. 0096151, and the like, all of which are hereby incorporated by reference. As a result, a method using oxygen as an oxidant is adopted, that is, a method of mixing oxygen with carbon dioxide and ammonia, starting raw materials, to form about 1 to 3 nm of a passivation film comprising hydroxides of Fe and Cr and an oxide of Cr at high temperature and high pressure.

But, when the amount of oxygen fed as an oxidant is too large, inert gases increase, and the H/C ($H_2O/CO_2$) ratio described later increases, and the reaction yield decreases.

On the other hand, an energy-consuming scrubber for finally separating and removing oxygen from unconverted raw materials and other volatile components, and a hydrogen combustion removal apparatus for preventing a risk that a trace amount of hydrogen contained in the urea product and oxygen are mixed are also required. In this manner, a problem of oxygen is that with an increase in feed, the corrosion resistance is increased, and on the other hand, the running cost is adversely affected.

Therefore, formerly, as noted in austenitic stainless steel S31603 series described in U.S. Pat. No. 2,680,766, development has been advanced in the direction of increasing the corrosion resistance of stainless steel itself. With this, improvements in workability required for apparatus production have also been made. As disclosed in British Patent No. 1,192,044, European Patent No. 0096151, International Publication No. WO 95/00674, British Patent No. 775,933, International Publication No. WO 03/018861, Japanese Patent Laid-Open No. 2003-301241, and the like, all of which are hereby incorporated by reference, improvements are made paying attention to the effects of Cr, Ni, Mo, and N. Particularly, International Publication No. Wo 03/018861 proposes austenite-ferrite duplex stainless steel having a Cr content of 28 to 35 wt %, a Ni content of 3 to 10 wt %, a Mo content of 1.0 to 4.0 wt %, and a N content of 2.0 to 0.6 wt %, suggesting that the construction of a urea synthesis plant that hardly requires corrosion prevention oxygen is possible.

But, a problem is that the material price of austenite-ferrite duplex stainless steel having excellent corrosion resistance and high Cr content in this manner is high and the construction cost of a urea plant increases, and the construction of a urea synthesis apparatus having both reliability and productivity is difficult.

Therefore, as disclosed in British Patent No. 1,341,497, British Patent No. 1,287,710, Japanese Patent Laid-Open No. 53-14993, Japanese Patent Laid-Open No. 56-131558, Japanese Patent Laid-Open No. 60-209555, Japanese Patent Laid-Open No. 10-182587, Japanese Patent Laid-Open No. 11-180942, and the like, all of which are hereby incorporated by reference, improvements in the production process and the apparatus have also been performed. Particularly, effectively recycling unreacted products by the introduction of a stripper, and providing to the condenser a urea synthesis function similar to that of the reactor increase the reaction yield, can make the production equipment small, and can contribute to the enhancement of productivity.

When the conventional art as described above is comprehensively considered, it is summarized into two types of urea synthesis methods. One uses expensive stainless steel having high Cr content and excellent corrosion resistance, and therefore, the apparatus can be operated at extremely low oxygen concentration, but a large burden is placed on the construction cost. For example, when austenite-ferrite duplex stainless steel having a Cr content of 28 to 35 wt %, a Ni content of 3 to 10 wt %, a Mo content of 1.0 to 4.0 wt %, and a N content of 0.2 to 0.6 wt % as disclosed in the above-described International Publication No. WO 03/018861 is used, the apparatus, including the stripper in which corrosion proceeds most easily, can be operated in a state in which oxygen is hardly required. But, the stainless steel is expensive, and a large burden is placed on the construction cost. The other uses general-purpose stainless steel such as S31603, and therefore, the burden of construction cost decreases, but the reaction yield is low, accessory equipment such as a scrubber for separating oxygen and a hydrogen combustion removal apparatus for removing hydrogen is required, and the construction cost and the running cost increase. For example, U.S. Pat. No. 2,727,069 discloses that in a urea synthesis plant using S31603 series general-purpose stainless steel, an oxygen concentration as much as about 1,000 to 30,000 ppm with respect to carbon dioxide is required. In addition, British Patent No. 1,341, 497also discloses that in a similar urea synthesis plant using S31603 series stainless steel, an oxygen concentration of 1,000 to 25,000 ppm with respect to carbon dioxide is required in the stripper, and an oxygen concentration of 300 to 10,000 ppm with respect to carbon dioxide is also required in the condenser.

In U.S. Pat. No. 3,137,724, it is described that a urea synthesis plant using S31603 series stainless steel can be operated at an oxygen concentration of 100 to 500 ppm with respect to carbon dioxide, and in British Patent No. 1,192, 044, it is described that urea synthesis plant using S31260 series stainless steel can be operated at an oxygen concentration of 100 to 500 ppm with respect to carbon dioxide. But, the oxygen concentration is oxygen concentration in the urea synthesis tower in which the progress of corrosion is slower than in the stripper, and there is no description regarding a stripper.

In addition, European Patent No. 0096151 also proposes that S31260 series stainless steel is used, and the apparatus can be operated with feed at an oxygen concentration of 200 to 2,000ppm with respect to carbon dioxide from the lower portion of the stripper. But, hydrogen peroxide is mixed into the upper portion of the reactor R in the synthesis system, oxygen is mixed into the lower portion, and hydrogen peroxide is mixed into the synthesis gas from the reactor R in the stripper S1. Oxygen is introduced into the bottom of the stripper S2, but it is necessary to introduce hydrogen peroxide from the top in order to compensate for an increase in the amount of gas due to stripping and a relative decrease in oxygen partial pressure at the top. The gas exiting the stripper S2 is condensed in the condenser C, and only the liquid phase portion is fed to the reactor, and the gas phase portion is vented from the upper portion of the condenser C. The oxygen introduced from the bottom of the stripper S2 and the oxygen in the hydrogen peroxide introduced from the upper portion transition to the gas phase portion to be vented, produced in the condenser C. Therefore, the oxygen introduced in a stripper S2 is hardly introduced into the reactor R, and therefore, it is necessary to separately introduce oxygen for passivation the metal surface of the reactor. Therefore, in the process disclosed in European Patent No. 0096151, oxygen must be introduced in a plurality of parts.

As described above, in the conventional art, a urea synthesis method satisfying reliability and productivity having a balance of the oxygen concentration required for corrosion resistance, the material of stainless steel, and an efficient production process is not found.

CITATION LIST

Patent Literature

Patent Literature 1: U.S. Pat. No. 2,680,766
Patent Literature 2: U.S. Pat. No. 2,727,069
Patent Literature 3: U.S. Pat. No. 3,137,724
Patent Literature 4: British Patent No. 1,153,107
Patent Literature 5: European Patent No. 0096151
Patent Literature 6: British Patent No. 1,192,044
Patent Literature 7: International Publication No. WO 95/00674
Patent Literature 8: International Publication No. WO 03/018861
Patent Literature 9: Japanese Patent Laid-Open No. 2003-301241
Patent Literature 10: British Patent No. 1,341,497
Patent Literature 11: British Patent No. 1,287,710
Patent Literature 12: Japanese Patent Laid-Open No. 53-149930
Patent Literature 13: Japanese Patent Laid-Open No. 56-131558
Patent Literature 14: Japanese Patent Laid-Open No. 60-209555
Patent Literature 15: Japanese Patent Laid-Open No. 10-182587
Patent Literature 16: Japanese Patent Laid-Open No. 11-180942, all of which are hereby incorporated by reference.

SUMMARY OF INVENTION

Technical Problem

It is an object of the present invention to provide a urea synthesis method using oxygen as an oxidant for forming passivity in order to protect a metal surface inside an apparatus from corrosive ammonium carbamate produced as a reaction intermediate in the synthesis of urea, using stainless steel as an apparatus material, and having excellent reliability and productivity.

More specifically, it is an object of the present invention to provide a urea synthesis method having excellent reliability and productivity in which the urea synthesis apparatus of interest has a process having improved synthesis ability involved by being provided with a condenser, and further, oxygen fed as an oxidant (hereinafter described as corrosion prevention oxygen) is the required minimum and the anticorrosiveness is excellent though inexpensive general-purpose stainless steel is selected as the material, and furthermore, urea can be produced at high reaction yield, low construction cost, and low cost.

Solution to Problem

The present invention is a urea synthesis method which (1) uses a urea synthesis apparatus for reacting ammonia with carbon dioxide at urea synthesis temperature and pressure in a urea synthesis tower, bringing a produced urea synthesis liquid comprising at least urea, unreacted ammonia and carbon dioxide, and water into contact with at least some raw material carbon dioxide under heating at a pressure substantially equal to the urea synthesis pressure in a stripper to separate the unreacted ammonia and the unreacted carbon dioxide as a mixed gas of ammonia, carbon dioxide, and water, and further treating the urea synthesis liquid containing unseparated unreacted ammonia and unreacted carbon dioxide to obtain urea, and, on the other hand, introducing the mixed gas separated in the stripper into a bottom of a condenser to bring the mixed gas into contact with an absorbing medium under cooling to condense the mixed gas, and circulating a thus obtained condensate to the urea synthesis tower, and in which (2) general-purpose austenitic-ferritic duplex stainless steel with Cr content: 21 to 26 wt %, Ni content: 4.5 to 7.5 wt %, Mo content: 2.5 to 3.5 wt %, N content: 0.08 to 0.30 wt %, C content: 0.03 wt % or less, Si content: 1.0 wt % or less, Mn content: 2.0 wt % or less, P content: 0.04 wt % or less, and S content: 0.03 wt % or less, for example, general-purpose S31803 or S31260, is applied as a urea synthesis apparatus material in at least a part of the urea synthesis tower, the stripper, the condenser, and a piping, the piping connecting at least two of the urea synthesis tower, the stripper, and the condenser with each other, and (3) the urea synthesis apparatus is operated with oxygen feed concentration with respect to carbon dioxide set to preferably 100 to 2,000 ppm, further preferably 100 to 1,000 ppm, and still further preferably 100 to 500 ppm, including the stripper. However, when only general-purpose austenitic-ferritic duplex stainless steel is used, the above lower limit values are each preferably 150 ppm or more.

The austenitic-ferritic duplex stainless steel further preferably has Cr content: 24 to 26 wt %, Ni content: 5.5 to 7.5 wt %, Mo content: 2.5 to 3.5 wt %, N content: 0.08 to 0.30 wt %, C content: 0.03 wt % or less, Si content: 1.0 wt % or less, Mn content: 1.5 wt % or less, P content: 0.04 wt % or less, and S content: 0.03 wt % or less.

In addition, the present invention is a urea synthesis method in which austenite-ferrite duplex stainless steel with Cr content: 26 to 35 wt %, Ni content: 3 to 10 wt %, Mo content: 1.0 to 4.0 wt %, and N content: 0.2 to 0.6 wt %, for example, S32707 or S32808, is used for a stripper, general-purpose austenitic-ferritic duplex stainless steel with Cr content: 21 to 26 wt %, Ni content: 4.5 to 7.5 wt %, Mo content: 2.5 to 3.5 wt %, N content: 0.08 to 0.30 wt %, C content: 0.03 wt % or less, Si content: 1.0 wt % or less, Mn content: 2.0 wt % or less, P content: 0.04 wt % or less, and S content: 0.03 wt % or less, for example, general-purpose S31803 or S31260, is used in at least a part of a urea synthesis tower, a condenser, and a piping, the piping connecting the urea synthesis tower and the condenser with each other, and a urea synthesis apparatus is operated with oxygen feed concentration with respect to carbon dioxide set to 100 to 500 ppm.

Advantageous Effects of Invention

According to the present invention, general-purpose austenitic-ferritic duplex stainless steel having Cr content: 21 to 26 wt %, Ni content: 4.5 to 7.5 wt %, Mo content: 2.5 to 3.5 wt %, N content: 0.08 to 0.30 wt %, a C content of 0.03 wt % or less, a Si content of 1.0 wt % or less, Mn content: 2.0 wt % or less, P content: 0.04 wt % or less, and S content: 0.03 wt % or less, for example, general-purpose S31803 or S31260, is applied as a urea synthesis apparatus material, and therefore, the present invention is effective in being able to reduce the cost of the material significantly and reduce the construction cost of the urea synthesis apparatus.

Moreover, the amount of oxygen fed as corrosion prevention oxygen for forming passivity to provide corrosion resistance is small, and therefore, inert gases decrease, the H/C ($H_2O/CO_2$) ratio described later decreases, and the reaction yield is enhanced. With this, since the amount of corrosion prevention oxygen is extremely small, compared with conventional urea synthesis apparatuses, not only is an energy-consuming scrubber for removing oxygen not required, but also a hydrogen combustion removal apparatus is not required because a risk that a trace amount of hydrogen contained in the produced urea is mixed with oxygen can be prevented. Therefore, the present invention is effective in being able to reduce the size of the entire apparatus and the equipment cost and also reduce the urea production cost without impairing reliability.

In addition, as described later, when Cr content: 26 to 35 wt %, Ni content: 3 to 10 wt %, Mo content: 0.2 to 4.0 wt %, N content: 0.2 to 0.6 wt %: austenite-ferrite duplex stainless steel, for example, S32707 or S32808, is used only for the stripper in which corrosion proceeds easily, the amount of corrosion prevention oxygen can be further reduced, and the running cost can be reduced.

Further, when a conventional case where corrosion prevention oxygen of about 5,000 ppm in terms of the volume of oxygen in raw material carbon dioxide is mixed is compared with a case where corrosion prevention oxygen is mixed in the range of the present invention, the synthesized two-phase flow condenses easily due to a decrease in the amount of corrosion prevention oxygen, and therefore, the heat transfer area of the condenser can be reduced by 5 to 10%. In addition, by decreasing corrosion prevention oxygen, the temperatures of the urea synthesis tower and the condenser can each be raised by 1 to 2° C., and the reaction rate can rise, increasing the reaction yield. Therefore, the amount of heat required of the stripper can be reduced by about 2 to 4%, and further, the shell diameters of the absorption tower and the washing tower following the synthesis loop can also be decreased by 15 to 30%. The reason why the amount of corrosion prevention oxygen is evaluated by concentration in raw material carbon dioxide is as follows. In the urea synthesis apparatus used in the present invention, the amount of raw material carbon dioxide is proportional to the urea production capacity of the urea synthesis apparatus, and therefore, it can be said that the amounts of gas and liquid in each site in the urea synthesis apparatus are proportional to the amount of raw material carbon dioxide. Therefore, evaluating the amount of corrosion prevention oxygen by concentration with respect to the amount of raw material carbon dioxide is equal to defining the amount of corrosion prevention oxygen with respect to the amounts of gas and liquid in each urea synthesis apparatus. Further, usually, in a urea apparatus, a compressor for corrosion prevention oxygen is not provided, and oxygen or air comprising oxygen is previously mixed with raw material carbon dioxide, and the pressure of the mixed gas is raised to urea synthesis system operating pressure by a carbon dioxide compressor. Therefore, in terms of operation management, by performing adjustment for keeping the proportion of oxygen flow rate (or air flow rate) to raw material carbon dioxide flow rate constant, an amount of oxygen of a defined value can be controlled. This method is extremely simple compared with a method of analyzing and evaluating gas at the inlet and outlet of each apparatus and reflecting the results in operation control. In the present invention, the amount of corrosion prevention oxygen mixed with raw material carbon dioxide and introduced is equal to the amount of corrosion prevention oxygen introduced into the entire urea synthesis apparatus. Therefore, the concentration of oxygen in each apparatus is obtained from this amount of corrosion prevention oxygen and the flow rate and partial pressure in each line. Therefore, the precision of analysis is also easily obtained.

On the other hand, the austenite-ferrite duplex stainless steel is the result of studying adoption mainly for the urea synthesis tower, the condenser, and the stripper. Further, by the adoption of general-purpose austenitic-stainless steel including S31603 series according to the corrosion environment such as piping and valves, it is also possible to further promote equipment cost reduction without increasing the amount of corrosion prevention oxygen.

In this manner, in the present invention, the materials of the apparatuses can be replaced, and therefore, the urea synthesis apparatus need not be a newly built plant the whole of which is newly constructed, and the present invention can also be applied to an enhanced plant (the so-called revamping) obtained by adding some portions to existing equipment or replacing some portions of existing equipment.

DESCRIPTION OF EMBODIMENTS

Figure 1:
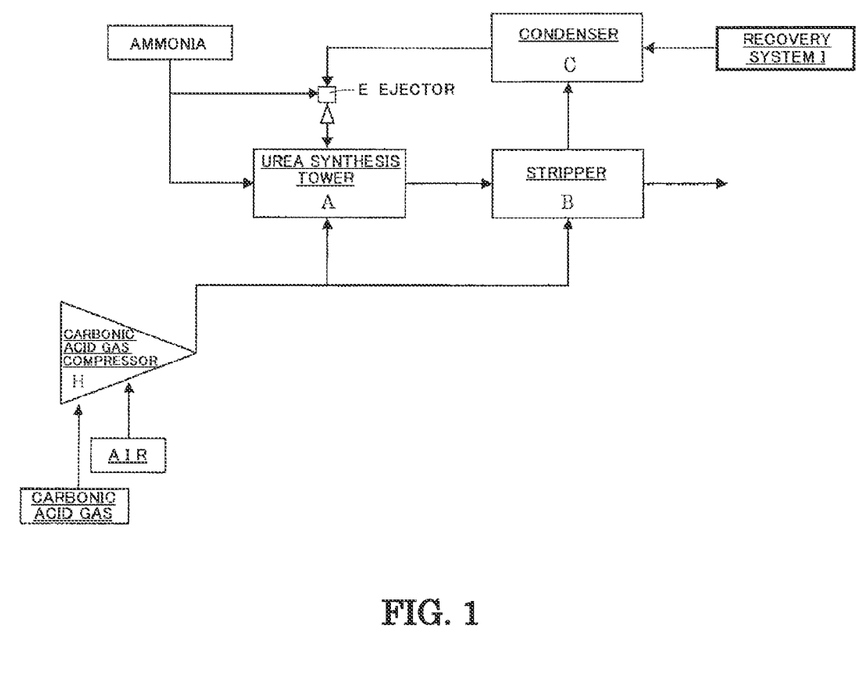
FIG. 1 is a process flow of a urea synthesis apparatus using a urea synthesis method with carbon dioxide stripping mode in the present invention.
Figure 2:
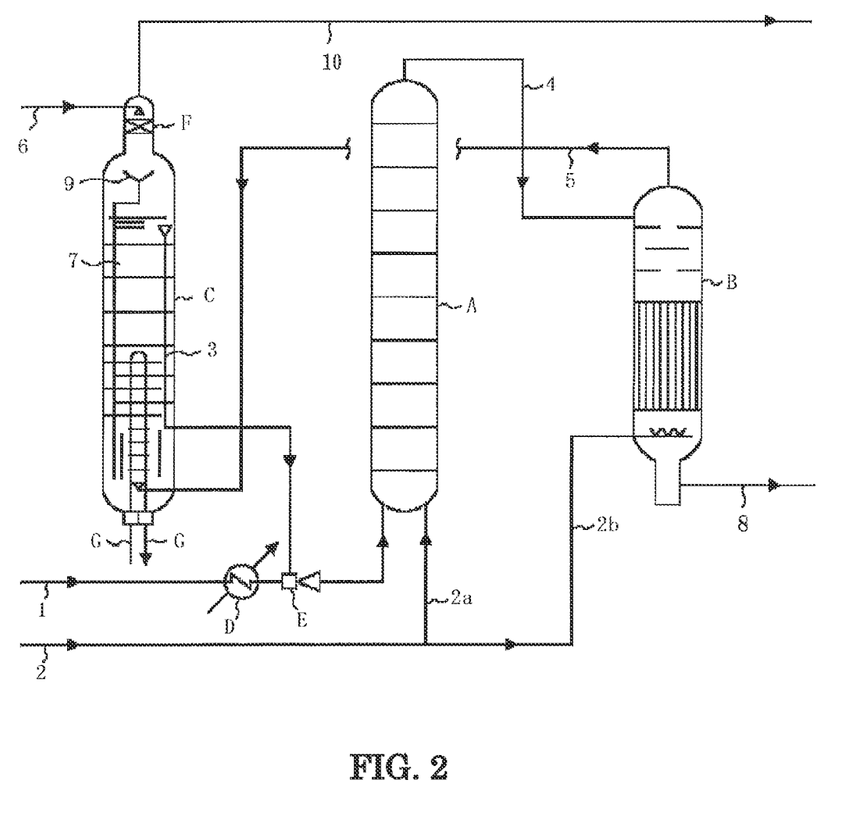
FIG. 2 is a process flow of a urea synthesis method disclosed in Japanese Patent Laid-Open No. 10-182587, which is one embodiment of a urea synthesis apparatus using the urea synthesis method with carbon dioxide stripping mode in the present invention.

One embodiment of the present invention is preferably the urea synthesis method with carbon dioxide stripping mode shown in FIG. 1, that is, a method of feeding raw material liquid ammonia to a urea synthesis tower A and feeding corrosion prevention oxygen as air together with raw material gaseous carbon dioxide to the urea synthesis tower A and a stripper B. Particularly, embodiments preferred as a urea synthesis method are various synthesis processes disclosed in Japanese Patent Laid-Open No. 10-182587, and one embodiment of them is shown in FIG. 2, but the urea synthesis method is not limited to this.

For example, the urea synthesis method may be in the form of feeding raw material liquid ammonia to the urea synthesis tower A and a condenser C and feeding raw material gaseous carbon dioxide comprising anticorrosive air fed from a carbonic acid gas compressor H only to the stripper B without feeding it to the urea synthesis tower A. In addition, for example, the urea synthesis method may be in the form of feeding raw material liquid ammonia to a recovery system I without feeding it to the urea synthesis tower A and feeding raw material gaseous carbon dioxide comprising corrosion prevention oxygen fed from a carbonic acid gas compressor H only to the urea synthesis tower A without feeding it to the stripper B (ammonia stripping mode). However, it should be noted that as shown in the conventional art, the pressure and temperature conditions and the compositions of remaining and passing fluids in regions such as the urea synthesis tower A, the stripper B, and the condenser C are different depending on the difference in the urea synthesis method, and therefore, a difference occurs in the amount of corrosion prevention oxygen required by stainless steel applied to the mode.

In addition, in the process flow in FIG. 1, for the purpose of raising the pressure of the liquid from the condenser C and circulating the synthesis liquid, from the viewpoint of a simple structure and excellent durability and maintenance, an ejector E is used, but other pressure raising means such as a pump can also be used for circulation. But, this may be omitted when the circulation of the urea synthesis liquid can be achieved well by the arrangement of the apparatuses. For example, when the arrangement of the apparatuses is devised, the urea synthesis liquid can be circulated only by gravity. However, when pressure raising means such as the ejector E is provided, the urea synthesis tower A, the condenser C, and the stripper B can be installed at low positions, which is preferred in installation work and maintenance. Further, the above apparatuses may be individually installed, or the condenser C and a scrubber or the like may be combined.

On the other hand, the orientation of the installation of the condenser may be horizontal or vertical. For example, when a horizontal condenser is installed on the ground or at a position close to the ground, combined with its low overall height, the installation work and maintenance of the urea synthesis tower are easy. The horizontal condenser is a pressure vessel comprising a hollow cylinder as a basic structure that is substantially horizontally installed, and usually, a plurality of baffles for preventing the back mixing and short path of liquid are vertically installed inside, and a disperser for dispersing gas is provided at the bottom. In addition, when a vertical condenser is used, not only can the installation area be saved, but gas-liquid countercurrent contact occurs in the condensation portion, and the residence time can be sufficiently long.

Further, the urea production apparatus used in the urea synthesis method of the present invention may be a newly built apparatus the whole of which is newly constructed or an enhanced apparatus (the so-called revamping) obtained by adding some portions to existing equipment or replacing some portions of existing equipment.

In such a urea synthesis apparatus, at least a part of the synthesis tower A, the stripper B, the condenser C, and a piping which connects at least two of the synthesis tower A, the stripper B, and the condenser C with each other can be of austenite-ferrite duplex stainless steel having the following composition.

[Composition of Austenite-Ferrite Duplex Stainless Steel Applied to Present Invention]

Cr: 21 to 26 wt %
Ni: 4.5 to 7.5 wt %
Mo: 2.5 to 3.5 wt %
N: 0.08 to 0.30 wt %
C: 0.03 wt % or less
Si: 1.0 wt % or less
Mn: 2.0 wt % or less
P: 0.04 wt % or less
S: 0.03 wt % or less
The Remainder is Fe and Impurities and Additives Particularly, S31803 and S31260, which are inexpensively available as general-purpose austenite-ferrite duplex stainless steel, are preferably used.

Further, as the austenite-ferrite duplex stainless steel, austenite-ferrite duplex stainless steel having the following composition is more preferably used.

[Composition of Austenite-Ferrite Duplex Stainless Steel Applied to Present Invention]

Cr: 24 to 26 wt %
Ni: 5.5 to 7.5 wt %
Mo: 2.5 to 3.5 wt %
N: 0.08 to 0.30 wt %
C: 0.03 wt % or less
Si: 1.0 wt % or less
Mn: 1.5 wt % or less
P: 0.04 wt % or less
S: 0.03 wt % or less
The Remainder is Fe and Impurities and Additives Particularly, S31260, which is inexpensively available as general-purpose austenite-ferrite duplex stainless steel, is preferably used.

Further, for the stripper in which corrosion proceeds easily, austenite-ferrite duplex stainless steel having the following composition is preferably used.

[Composition of Austenite-Ferrite Duplex Stainless Steel Applied to Present Invention]

Cr: 26 to 35 wt %
Ni: 3 to 10 wt %
Mo: 0.2 to 4.0 wt %,
N: 0.2 to 0.6 wt %

The Remainder is Fe and Impurities and Additives

Particularly, as such austenite-ferrite duplex stainless steel, for example, S32707 and S32808 are preferably used.

In addition, S31603 series general-purpose stainless steel can also be used according to the corrosion environment such as piping and valves, and it is also possible to further promote a reduction in equipment cost without increasing the amount of corrosion prevention oxygen.

The urea synthesis apparatus fabricated with the materials as described above is preferably mainly operated with the operating conditions of the urea synthesis tower A set to pressure: 130 to 250 bar, N/C: 3.5 to 5.0, H/C: 1.0 or less, residence time: 10 to 40 minutes, and temperature: 180 to 200° C., the operating conditions of the stripper set to pressure: 130 to 250bar, particularly preferably 140 to 200 bar, and temperature: 160 to 200° C., and the operating conditions of the condenser C set to pressure: 140 to 250 bar, temperature: 130 to 250° C., particularly preferably 170 to 190° C., N/C: 2.5 to 3.5, H/C: 1.0 or less, and residence time: 10 to 30 minutes, from the viewpoint of reaction yield. Here, N/C is the molar ratio of ammonia (including ammonia converted to ammonium carbamate and urea) to carbon dioxide (including carbon dioxide converted to ammonium carbamate and urea) (hereinafter referred to as "N/C"), and H/C is the molar ratio of water (excluding water produced in the urea synthesis reaction) to carbon dioxide (including ammonium carbamate and carbon dioxide converted to urea) (hereinafter referred to as "H/C").

Such operating conditions are preferred based on the fact that as shown in FIG. 1, not only do reactions of the following equation 1 and equation 2 occur in the urea synthesis tower A, but the reactions proceed also in the condenser C while ammonia gas and/or carbon dioxide gas are condensed. Equation 1 is a reaction in which ammonium carbamate ($NH_2CO_2NH_4$) is produced by the reaction of ammonia ($NH_3$) with carbon dioxide ($CO_2$). Equation 2 is an equilibrium reaction in which urea ($CO(NH_2)_2$) is produced by the dehydration reaction of ammonium carbamate ($NH_2CO_2NH_4$).

[Formula 1]

$$2NH_3 + CO_2 \rightarrow NH_2CO_2NH_4 \text{ (exothermic reaction)} \quad \text{equation 1}$$

$$NH_2CO_2NH_4 \leftrightarrow CO(NH_2)_2 + H_2O \text{ (endothermic reaction)} \quad \text{equation 2}$$

In other words, in FIG. 1, the pressure of raw material liquid ammonia is raised to the desired pressure by an ammonia pump (not shown), and the raw material liquid ammonia is fed to the urea synthesis tower A, and some of the raw material liquid ammonia is heated by a heat exchanger and also fed to the ejector E, and on the other hand, a urea synthesis liquid is fed to the ejector E also from the condenser C, and from this ejector E, the pressure of the urea synthesis liquid comprising ammonia is raised, and the urea synthesis liquid is fed to the urea synthesis tower A. The pressure of raw material gaseous carbon dioxide is raised to the desired pressure by the carbonic acid gas compressor H, and most of the raw material gaseous carbon dioxide is fed to the stripper B. Some of the remaining carbon dioxide is fed to the urea synthesis tower A for the purposes of the temperature control of the urea synthesis tower A and feeding corrosion prevention oxygen. As the corrosion prevention oxygen, usually air is fed to the first-stage suction side or intermediate stage of the carbonic acid gas compressor H. Urea is synthesized in the urea synthesis tower A and the condenser C, and the effluent comprising urea exiting the urea synthesis tower A is fed to the stripper B. In this effluent, synthesized urea, water, ammonium carbamate, and unreacted ammonia are present as a liquid phase, and some unreacted ammonia and carbon dioxide together with inert gases are present as a gas phase. Here, the term inert gases is a general term for impurities such as hydrogen and nitrogen contained in raw material carbon dioxide and anticorrosive air introduced for preventing the corrosion of the urea synthesis apparatus composed of, for example, the urea synthesis tower A, the stripper B, the condenser C, a scrubber, and piping coupling them. The synthesis liquid from the urea synthesis tower A is fed to the stripper B, and here, the unreacted ammonia and the unreacted carbon dioxide are treated. The raw material carbon dioxide is used as a stripping agent.

Therefore, the operating conditions of the urea synthesis tower A, the stripper B, and the condenser C in the production apparatus as shown in FIG. 1 are determined by the reasons shown below, including Le Chatelier's principle.

First, the pressure inside the urea synthesis tower A is preferably 130 to 250 bar. When this synthesis pressure is 130 bar or more, an operating pressure allowing a margin for a synthesis equilibrium pressure at a temperature preferred for the synthesis of urea (180° C. or more) can be adopted, and moreover, a decrease in reaction yield due to gasification can be prevented. In addition, when the synthesis pressure is 250 bar or less, the energy for raising the pressure of raw material ammonia, raw material carbonic acid gas, and an unreacted ammonium carbamate liquid can be suppressed, and the equipment cost can be reduced. Here, the ammonium carbamate liquid is a liquid obtained by recovering unreacted ammonia and carbon dioxide as an aqueous solution of ammonium carbamate in the recovery step downstream from the synthesis step.

Next, for the synthesis temperature inside the urea synthesis tower A, as it becomes higher, the reaction of equation 1 proceeds to the left side, and the reaction of equation 2 proceeds to the right side. Therefore, a region suitable in terms of reaction yield is present, and the synthesis temperature is preferably 180° C. to 200° C. When this synthesis temperature is 180° C. or more, a slow reaction rate of urea production can be prevented. In addition, when the synthesis temperature is 200° C. or less, a high risk of the so-called active corrosion in addition to an increase in corrosion rate can be prevented. This synthesis temperature can be controlled, for example, by the preheating temperature of ammonia for driving the ejector E and/or the amount of carbon dioxide fed to the urea synthesis tower A.

N/C inside the urea synthesis tower A is stoichiometrically 2 from equation 1, but a state in which excess unreacted ammonia is present is preferred. But, when N/C exceeds 5.0, the ammonia vapor pressure increases, and a gas phase is easily produced, and therefore, N/C is preferably 3.5 to 5.0.

For H/C inside the urea synthesis tower A, lower H/C is good from equation 1 and equation 2 from the viewpoint of reaction yield. Therefore, the amount of water fed to this recovery apparatus is preferably the required minimum. H/C is preferably 1.0 or less, further preferably 0.7 or less, and still further preferably 0.4 or less because it is better that this H/C can be decreased as much as possible, but H/C is often determined by the amount of water required for the absorption of unreacted materials (ammonia and carbon dioxide) exiting the urea synthesis apparatus in the recovery apparatus for recovering the unreacted materials (not shown), and actually, some amount of water is present. It is not necessary to set the lower limit of H/C.

The residence time of the urea synthesis liquid inside the urea synthesis tower A is preferably 10 minutes or more and 40 minutes or less. When this residence time is 10 minutes or more, the progress of the urea synthesis reaction is promoted. On the other hand, when a residence time exceeding 40 minutes is set, a further rise in reaction yield can be hardly expected because the reaction yield already reaches close to equilibrium reaction yield.

In the above operating conditions, the reaction yield is about 60% or more and about 75% or less inside the urea synthesis tower A. Here, the reaction yield based on carbon dioxide is the ratio between the number of moles of carbon dioxide fed to an apparatus or a region to be considered and the number of moles of carbon dioxide converted to urea, of the fed carbon dioxide, and is usually expressed in %.

The operating conditions of the stripper B are required to promote the reverse reaction of equation 1. Basically, higher temperature and lower pressure are preferred. From the balance of the entire urea synthesis apparatus, the operating conditions of the stripper B are set to pressure: 130 to 250 bar, particularly preferably 140 to 200 bar, and temperature: 160 to 200° C.

The operating conditions of the condenser C can be considered as in the urea synthesis tower A because synthesis ability is provided to the condenser C. A reaction yield of 20 to 60% can be achieved under substantially the same conditions as the urea synthesis tower A, that is, pressure: 140 to 250 bar, temperature: 130 to 250° C., particularly preferably 170 to 190° C., N/C: 2.5 to 3.5, H/C: 1.0 or less, and residence time: 10 to 30 minutes.

Under such a synthesis apparatus and operating conditions, corrosion prevention oxygen for the apparatus is fed as air simultaneously with carbon dioxide as shown in FIG. 1. The required amount of corrosion prevention oxygen is different among the apparatuses, the urea synthesis tower A, the stripper B, and the condenser C. The stripper B is in the most easily corroded environment followed by the condenser and the urea synthesis tower in order. But, in the synthesis apparatus used in the present invention, corrosion prevention oxygen is distributed throughout the synthesis apparatus, and therefore, the amount of corrosion prevention oxygen is determined by the minimum oxygen feed required in the stripper, and preferably 100 to 2,000 ppm, further preferably 100 to 1,000 ppm, of corrosion prevention oxygen is required. In addition, by selecting the material of stainless steel used in each portion of the synthesis apparatus, the synthesis apparatus can be operated with a further preferred amount of corrosion prevention oxygen of 100 to 500 ppm. However, when only general-purpose austenitic-ferritic duplex stainless steel is used, the above lower limit values are each preferably 150 ppm or more.

Particularly, when such austenite-ferrite duplex stainless steel as to have Cr content: 26 to 35 wt %, Ni content: 3 to 10 wt %, Mo content: 1.0 to 4.0 wt %, and N content: 0.2 to 0.6 wt %, for example, S32707 or S32808, is used for the stripper in which corrosion proceeds easily, the oxygen feed concentration with respect to carbon dioxide can be reduced to 100 to 500 ppm.

For the method for feeding this corrosion prevention oxygen, it is preferred that anticorrosive air is mixed into raw material carbon dioxide and fed as shown in the process flow in FIG. 1 from the viewpoint that it is not necessary to newly provide a pressure raising apparatus. But, the present invention is not limited to this feeding method. For example, the apparatuses may be individually provided with an introduction port for anticorrosive air and an apparatus for raising pressure to a predetermined pressure, to feed anticorrosive air to each apparatus. Also in this case, corrosion prevention oxygen is distributed throughout the synthesis apparatus, and therefore, the amount of anticorrosive air fed, that is, the corrosion prevention oxygen concentration, remains unchanged.

By decreasing corrosion prevention oxygen in this manner, the gas composition is outside the explosion range, and a hydrogen combustion removal apparatus can be omitted, but it may be installed for safety. When the hydrogen combustion removal apparatus is installed, it is preferably at the middle stage or outlet of the carbon dioxide compressor downstream of anticorrosive air, or upstream from the stage of introducing carbon dioxide in the stripper because hydrogen can be removed by catalyst combustion in the hydrogen removal apparatus using some of the introduced corrosion prevention oxygen, and these places are before the explosion range under high temperature conditions like the stripper.

EXAMPLES

The present invention will be described more specifically and more intelligibly below by Examples.

Figure 3:
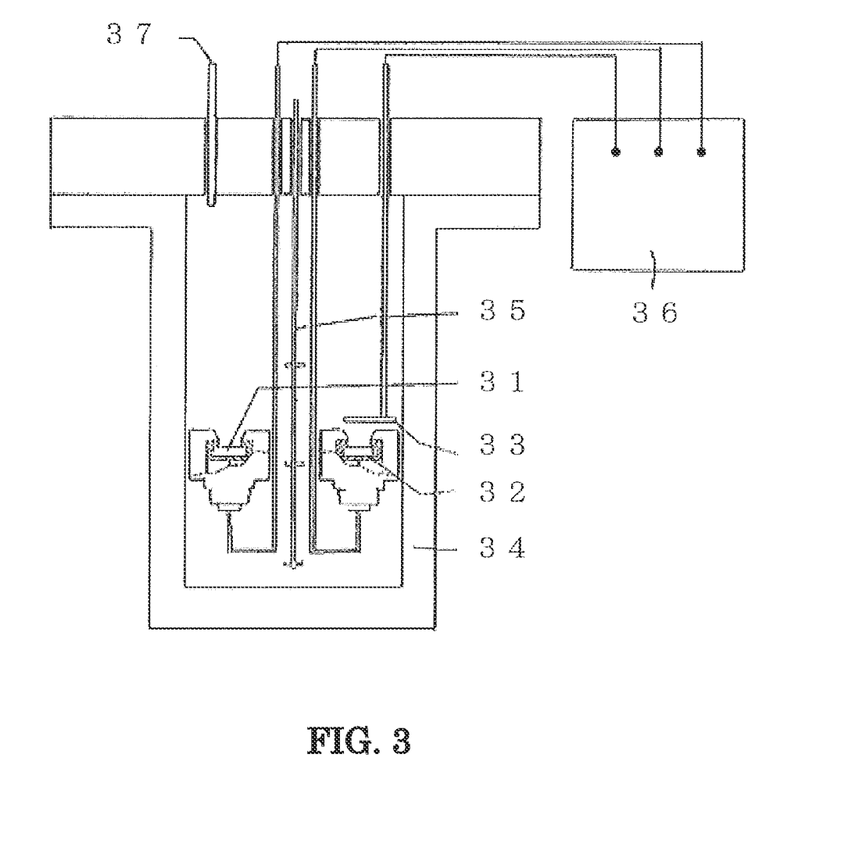
FIG. 3 is a schematic view showing a measurement apparatus used in an experiment.

A test was carried out under the following conditions using the measurement apparatus shown in FIG. 3. The measurement apparatus shown in FIG. 3 comprises an autoclave (34) for synthesizing urea, and an electrochemical measurement apparatus for measuring the corrosion behavior of a material. Three electrodes [a working electrode (31), a reference electrode (32) comprising Pt, and a counter electrode (33) comprising Pt] are installed in the autoclave (34), and the control and measurement of the potential between the electrodes and the measurement of current are carried out using a potentiostat module (36). In addition, a urea synthesis liquid is stirred by an agitator (35), and anticorrosive air (corrosion prevention oxygen) is fed from an air feed nozzle (37).

Figure 4:
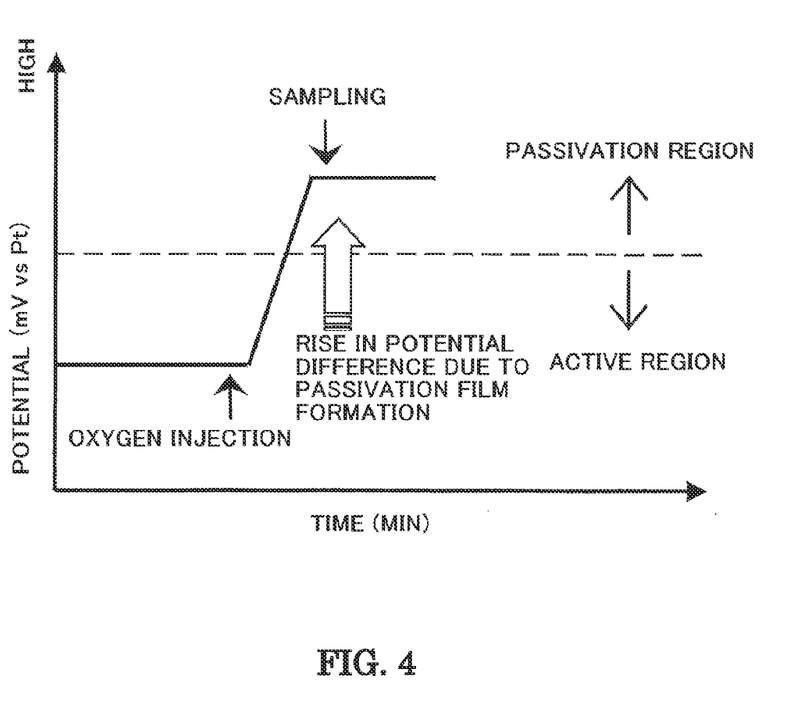
FIG. 4 is a schematic graph showing the measurement principle in the measurement apparatus used in the experiment.

The relationship between the principle of this measurement and anticorrosive performance due to passivation film formation is schematically shown in FIG. 4. In other words, the corrosion behavior of the working electrode (31) can be grasped by the potential difference (natural potential) occurring between the working electrode (31) and the reference electrode (32) immersed in a urea synthesis liquid synthesized in the autoclave (34). It is shown that when the potential difference between both is small, a sufficient passivation film is not formed on the working electrode (31), and the electrode is actively dissolved, whereas when the potential difference is large, passivation occurs. Therefore, by analyzing the synthesis gas sampled immediately after a rise in potential difference, the corrosion prevention oxygen concentration required for passivation can be grasped.

An experimental method will be show below.
[Stainless Steel Materials]
Austenite-ferrite duplex stainless steel: S31260 (manufactured by Sumitomo Metal Industries, Ltd.)
Austenite-ferrite duplex stainless steel: S32808 (manufactured by Sumitomo Metal Industries, Ltd.)
Austenitic stainless steel: S31603 (manufactured by Sumitomo Metal Industries, Ltd.)

[Experimental Apparatuses]

Autoclave: manufactured by Nitto Koatsu Co., Ltd./custom-made product

Aspirator: manufactured by EYELA/A-1000S

Current-potential measurement apparatus (potentiostat): manufactured by HOKUTO DENKO CORPORATION/HA-151B Gas chromatography: manufactured by SHIMADZU CORPORATION/GC-14A

[Test]

(1) Water, ammonium carbonate, and urea are placed in the autoclave (34).

(2) The autoclave (34) is covered with a lid, and then, the autoclave (34) is degassed by the aspirator.

(3) He replacement (1 MPa×5 times) is performed to remove oxygen inside the autoclave (34).

(4) Ammonia is fed into the autoclave (34).

(5) H/C=4 and H/C=1 are set, and the temperature is set to 195° C. At this time, the pressure was about 160 bar.

(6) After the temperature is raised to 195° C., the corrosion rate during passivation is measured by a polarization resistance method.

(7) Cathode treatment (−0.8 V/5 min) is carried out to remove the passivation film on the surface.

(8) After the potential difference between the working electrode (31) and the reference electrode (32) was low, showing the active region, the current flowing between the working electrode (31) and the counter electrode (33) was measured by the polarization resistance method. The corrosion rate during active dissolution was obtained from this current value.

(9) Air is fed into the autoclave (34) from the air feed nozzle (37) in the state of the active region.

(10) It is confirmed that the potential reaches the passivation region.

(11) The corrosion rate is measured by the polarization resistance method.

(12) The gas in the autoclave (34) is sampled.

(13) The sampled gas is analyzed by gas chromatography, and the oxygen concentration is confirmed.

(14) This amount of oxygen is taken as the amount of oxygen required for the passivation of the material.

[Simulation and Results]

The apparatus in FIG. 2 is described in detail in Japanese Patent Laid-Open No. 10-182587, and the process flow will be briefly described. Raw material liquid ammonia enters a heat exchanger D from a line 1 at a pressure of 150 to 300 bar, is preheated to 100 to 200° C. here, and enters an ejector E as a driving fluid. The raw material liquid ammonia is expanded through the ejector E so that the differential pressure between the discharge pressure and suction pressure of the ejector is 2 to 10 bar. Thus, a condensate fed to the suction side of the ejector E through the down pipe 3 of a condenser C is sucked, and the pressure is raised. The condensate is introduced into the bottom of a urea synthesis tower A as a mixture with the raw material liquid ammonia, the driving fluid. Of raw material carbon dioxide, the amount of raw material carbon dioxide required for carbon dioxide stripping is fed to the bottom of a stripper B through lines 2 and 2b, and the remaining amount of raw material carbon dioxide is fed to the bottom of the urea synthesis tower A through a line 2a. The mixture of the raw material liquid ammonia and the condensate from the ejector E and the carbon dioxide fed from the line 2a react while rising in the urea synthesis tower A. The operating conditions of the urea synthesis tower A are set to pressure: 130 to 250 bar, N/C: 3.5 to 5.0, H/C: 1.0 or less, residence time: 10 to 40 minutes, and temperature: 180 to 200° C. A urea synthesis liquid comprising urea, unreacted ammonia, unreacted carbon dioxide, and water produced in the urea synthesis tower A is drawn out from the top of the urea synthesis tower and fed to the top of the stripper B at a pressure substantially equal to or slightly lower than the pressure of the urea synthesis tower through a line 4. This urea synthesis liquid is brought into contact with the raw material carbon dioxide fed to the bottom of the stripper B through the line 2b under heating while flowing down the stripper B, and the unreacted ammonia and the unreacted carbon dioxide are separated as a mixed gas of ammonia, carbon dioxide, inert gases, and water. This mixed gas is introduced into the bottom of the condenser C from the top of the stripper B through a line 5. Anticorrosive air is mixed with the raw material carbon dioxide for stripping and introduced into the stripper B. The operating conditions of the stripper are set to pressure: 130 to 250 bar and temperature: 160 to 200° C. The urea synthesis liquid comprising unseparated unreacted ammonia and unreacted carbon dioxide is drawn out from the bottom of the stripper B through a line 8, fed to a low pressure decomposition step, and treated, and urea is obtained. A scrubber F is integrated at the top of the condenser C. A recovered liquid from a low pressure recovery step (not shown) is fed as an absorbing medium to the top of the scrubber F through a line 6. This absorbing medium comes into contact with the inert gases from the condenser C and absorbs and removes the ammonia and the carbon dioxide entrained in the inert gases. The inert gases are released through a line 10. On the other hand, the absorbing liquid (the absorbing medium absorbing the ammonia and the carbon dioxide entrained in the inert gases) from the scrubber F flows down to a receiver 9 provided at the bottom of the scrubber F, flows down a down pipe 7, and becomes an absorbing medium for the mixed gas from the stripper at the bottom of the condenser C. The above absorbing medium for the mixed gas from the stripper comes into contact with the above mixed gas and condenses this under cooling by a cooler G. The produced condensate rises in the condenser C, is fed to the suction side of the ejector E through a down pipe 3 having an opening at the top, and fed to the bottom of the urea synthesis tower A together with raw material liquid ammonia as described above. The operating conditions of the condenser C are substantially the same as those of the urea synthesis tower A and are set to pressure: 140 to 250 bar, temperature: 130 to 250° C., N/C: 2.5 to 3.5, H/C: 1.0 or less, and residence time: 10 to 30 minutes.

Figure 5:
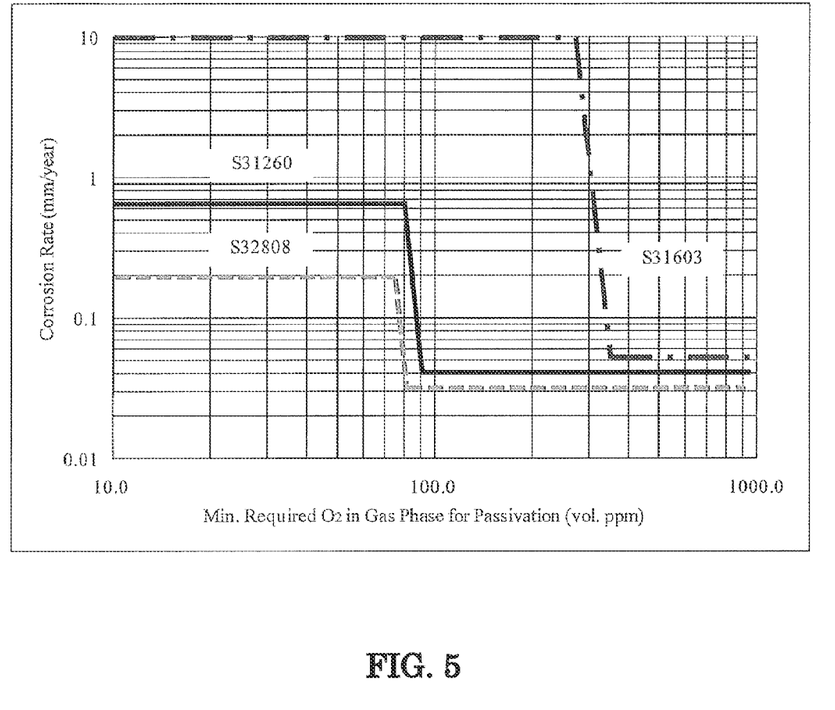
FIG. 5 shows measurement results obtained from the experiment.

In view of such operating conditions, the relationship between corrosion rate and oxygen concentration with respect to raw material carbon dioxide was obtained by the method shown below. First, the corrosion rate during passivation and during active dissolution and the amount of oxygen in the gas phase required for passivation are obtained for each material by the method shown in the paragraph 0059 (FIG. 5). Next, the oxygen concentration in the gas phase is obtained for each of the urea synthesis tower, the condenser, and the stripper using a process simulator for design, and the relationship with oxygen feed concentration with respect to raw material carbon dioxide is obtained. Using both, the relationship between corrosion prevention oxygen concentration with respect to raw material carbon dioxide and corrosion rate for each material in each apparatus is obtained.

Figure 6:
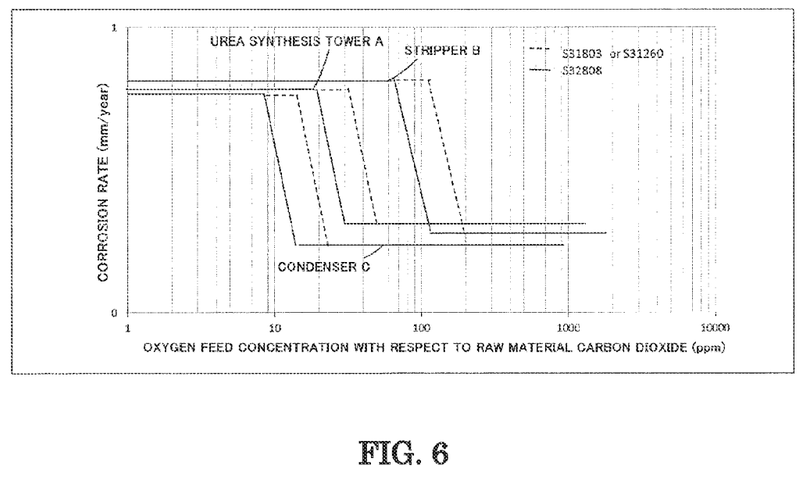
FIG. 6 shows simulation results based on the experimental results.

The results obtained in the paragraph 0061 are shown in FIG. 6. As is clear from these results, it is seen that even when the same general-purpose austenite/ferrite duplex stainless steel is used, the corrosion rates for the apparatuses of the urea synthesis tower A, the condense C, and the stripper B are different from each other, with respect to the corrosion prevention oxygen concentration in the raw material carbon dioxide, and the environment of the stripper is most severe. Therefore, since the total amount of corrosion prevention oxygen is distributed in the synthesis apparatus used in the present invention, the corrosion prevention The results are shown in Table 1. As is clear from Table 1, the heat transfer area of the condenser can be reduced by about 7 to 12%. At the same time, the temperatures of the urea synthesis tower A and the condenser C were each raised by 1 to 2° C., the reaction rate rose, the reaction yield was increased, and the amount of heat required of the stripper was reduced by about 4%.

TABLE 1

| | Mateirals | | | | Amount of anticorrosive oxygen [ppm-CO2] | Condenser heat transfer area [Relative ratio] | Amount of heat of stripper [Relative ratio] |
|---|---|---|---|---|---|---|---|
| | Piping and control valves | Reactor | Condenser | Stripper | | | |
| Comparative Example 1 | S 3 1 6 0 3 | S 3 1 6 0 3 | S 3 1 6 0 3 | S 3 1 6 0 3 | 5000 | 100 | 100 |
| Example 1 | S 3 1 2 6 0 | S 3 1 2 6 0 | S 3 1 2 6 0 | S 3 1 2 6 0 | 2000 | 93 | 96 |
| Example 2 | S 3 1 2 6 0 | S 3 1 2 6 0 | S 3 1 2 6 0 | S 3 1 2 6 0 | 1500 | 91 | 96 |
| Example 3 | S 3 1 2 6 0 | S 3 1 2 6 0 | S 3 1 2 6 0 | S 3 1 2 6 0 | 1000 | 88 | 96 |
| Example 4 | S 3 1 2 6 0 | S 3 1 2 6 0 | S 3 1 2 6 0 | S 3 2 8 0 8 | 500 | 88 | 96 |
| Example 5 | S 3 2 8 0 8 | S 3 2 8 0 8 | S 3 2 8 0 8 | S 3 2 8 0 8 | 500 | 88 | 96 | oxygen concentration required for the anticorrosion of the stripper is required at the minimum.

In other words, FIG. 6 shows that in the urea synthesis apparatus shown in FIG. 2, general-purpose austenitic-ferritic duplex stainless steel with Cr content: 21 to 26 wt %, Ni content: 4.5 to 7.5 wt %, Mo content: 2.5 to 3.5 wt %, N content: 0.08 to 0.30 wt %, C content: 0.03 wt % or less, Si content: 1.0 wt % or less, Mn content: 2.0 wt % or less, P content: 0.04 wt % or less, and S content: 0.03 wt % or less, for example, general-purpose S31803 or S31260, is used as a urea synthesis apparatus material in at least a part of the synthesis tower A, the stripper B, the condenser C, and a piping which connects at least two of the synthesis tower A, the stripper B, and the condenser C with each other, and an oxygen feed concentration of about 100 to 2,000 ppm with respect to carbon dioxide is required under the operating conditions of temperature: 195° C. and pressure: 160 bar. When only general-purpose austenitic-ferritic duplex stainless steel is used, the above lower limit value is preferably 150 ppm or more.

Therefore, when as the above stainless steel, such austenite-ferrite duplex stainless steel as to have Cr content: 26 to 35 wt %, Ni content: 3 to 10 wt %, Mo content: 0.2 to 4.0 wt %, and N content: 0.2 to 0.6 wt %, for example, S32707 or S32808, is used for the stripper, the oxygen feed concentration with respect to carbon dioxide can be decreased to 100 to 500 ppm.

On the other hand, the reduction in the amount of corrosion prevention oxygen can reduce condenser heat transfer area because the synthesized two-phase flow condenses easily due to the decrease in oxygen/air. In addition, by decreasing corrosion prevention oxygen, the temperature of the urea synthesis tower and the condenser can be raised, and it is expected that the reaction rate rises, increasing the reaction yield.

Combinations of the material used and the corresponding amount of corrosion prevention oxygen were determined based on the study shown in the paragraph 0061, and for the effects shown in the paragraph 0065, the condenser heat transfer area and the amount of heat of the stripper with respect to the amount of corrosion prevention oxygen for each stainless steel were evaluated by the above-described process simulator.

Reference Signs List
A Urea synthesis tower
B Stripper
C Condenser
D Heat exchanger
E Ejector
F Scrubber
G Cooler
H Carbonic acid gas compressor
I Recovery system
1 Ammonia feed line
2 Carbon dioxide feed line
3 Down pipe
4 Transmission line for a urea synthesis liquid comprising unreacted ammonia and unreacted carbon dioxide
5 Transmission line for a mixed gas comprising ammonia, carbon dioxide, inert gases, and water
6 Introduction line for a recovered liquid from a low pressure recovery step
7 Down pipe
8 Recovery line for a urea synthesis liquid comprising unreacted ammonia and unreacted carbon dioxide
9 Receiver
10 Inert gas discharge line
31 Working electrode
32 Reference electrode
33 Counter electrode
34 Autoclave
35 Agitator
36 Potentiostat module
37 Air feed nozzle

The invention claimed is:
1. A urea synthesis method using only oxygen previously mixed with raw material carbon dioxide as a corrosion-resistant agent forming a passivation film on a stainless steel surface in which:
 ammonia and the raw material carbon dioxide are reacted at a urea synthesis temperature and pressure in a urea synthesis tower in a urea synthesis apparatus to produce a urea synthesis liquid comprising at least urea, unreacted ammonia, unreacted carbon dioxide, and water;

contacting the urea synthesis liquid with at least some of the raw material carbon dioxide under heating at a pressure substantially equal to the urea synthesis pressure in a stripper to separate the unreacted ammonia and the unreacted carbon dioxide as a mixed gas of ammonia, carbon dioxide, and water;

further treating the urea synthesis liquid obtained in the stripper containing unseparated unreacted ammonia and unreacted carbon dioxide to obtain urea;

introducing the mixed gas separated in the stripper into a bottom of a condenser to bring the mixed gas into contact with an absorbing medium under cooling to condense the mixed gas; and circulating the mixed gas condensate to the urea synthesis tower, wherein a majority of the raw material carbon dioxide is fed into the stripper, and wherein a remaining portion of the raw material carbon dioxide is fed into the urea synthesis tower, and wherein a molar ratio of ammonia (including ammonia converted to ammonium carbamate and urea) to carbon dioxide (including carbon dioxide converted to ammonium carbamate and urea) in the condenser is 2.5 to 3.5, and wherein an oxygen concentration of the raw material carbon dioxide fed into both the stripper and the urea synthesis tower is 200 to 2,000 ppm, and wherein general-purpose austenitic-ferritic duplex stainless steel comprising Cr content: 21 to 26 wt %, Ni content: 4.5 to 7.5 wt %, Mo content: 2.5 to 3.5 wt %, N content: 0.08 to 0.30 wt %, C content: 0.03 wt % or less, Si content: 1.0 wt % or less, Mn content: 2.0 wt % or less, P content: 0.04 wt % or less, and S content: 0.03 wt % or less is used as the apparatus material in at least one of the synthesis tower, the stripper, the condenser, or a piping, wherein the piping connects at least two of the synthesis tower, the stripper, and the condenser with each other.

2. The urea synthesis method according to claim 1, wherein austenitic-stainless steel is used as the apparatus material of the synthesis tower, the condenser, the piping, and valves, wherein the piping connects the synthesis tower and the condenser with each other.

3. The urea synthesis method according to claim 2, wherein the general-purpose austenitic-ferritic duplex stainless steel is either S31803 or S31260, and the austenitic-stainless steel is S31603.

4. A urea synthesis method using only oxygen previously mixed with raw material carbon dioxide as a corrosion-resistant agent forming a passivation film on a stainless steel surface in which:

ammonia and the raw material carbon dioxide are reacted at a urea synthesis temperature and pressure in a urea synthesis tower in a urea synthesis apparatus to produce a urea synthesis liquid comprising at least urea, unreacted ammonia, unreacted carbon dioxide, and water;

contacting the urea synthesis liquid with at least some of the raw material carbon dioxide under heating at a pressure substantially equal to the urea synthesis pressure in a stripper to separate the unreacted ammonia and the unreacted carbon dioxide as a mixed gas of ammonia, carbon dioxide, and water;

further treating the urea synthesis liquid obtained in the stripper containing unseparated unreacted ammonia and unreacted carbon dioxide to obtain urea;

introducing the mixed gas separated in the stripper into a bottom of a condenser to bring the mixed gas into contact with an absorbing medium under cooling to condense the mixed gas; and circulating the mixed gas condensate to the urea synthesis tower, wherein a majority of the raw material carbon dioxide is fed into the stripper, and wherein a remaining portion of the raw material carbon dioxide is fed into the urea synthesis tower, and wherein a molar ratio of ammonia (including ammonia converted to ammonium carbamate and urea) to carbon dioxide (including carbon dioxide converted to ammonium carbamate and urea) in the condenser is 2.5 to 3.5, and wherein an oxygen concentration of the raw material carbon dioxide fed into both the stripper and the urea synthesis tower is 100 to 500 ppm, and wherein specific austenitic-ferritic duplex stainless steel comprising Cr content: 26 to 35 wt %, Ni content: 3 to 10 wt %, Mo content: 0.2 to 4.0 wt %, N content: 0.2 to 0.6 wt %, is used as the apparatus material of the stripper, and wherein general purpose austenitic-ferritic duplex stainless steel comprising Cr content: 21 to 26 wt %, Ni content: 4.5 to 7.5 wt %, Mo content: 2.5 to 3.5 wt %, and N content: 0.08 to 0.3 wt %, C content: 0.03 wt % or less, Si content: 1.0 wt % or less, Mn content: 2.0 wt % or less, P content: 0.04 wt % or less, and S content: 0.03 wt % or less is used as the apparatus material in at least one of the synthesis tower, the condenser, a piping, or valves, and wherein the piping connects the synthesis tower and the condenser with each other.

5. The urea synthesis method according to claim 4, wherein the specific austenitic-ferritic duplex stainless steel material is either S32707 or S32808 and the general-purpose austenitic-ferritic duplex stainless steel is either S31803 or S31260.

* * * * *